(12) United States Patent
Gielen et al.

(10) Patent No.: US 6,321,104 B1
(45) Date of Patent: Nov. 20, 2001

(54) BURR HOLE CAP FOR FIXATION OF CRANIAL LEAD

(75) Inventors: Frans L. H. Gielen, Eckelrade; W A. J. Elands, Oldenzaal, both of (NL)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 09/186,491

(22) Filed: Nov. 5, 1998

(51) Int. Cl.$^7$ ................................ A61N 1/02; A61N 1/05
(52) U.S. Cl. ............................. 600/378; 607/116
(58) Field of Search ................ 607/116; 606/129, 606/130; 600/378

(56) References Cited

U.S. PATENT DOCUMENTS

| | | | |
|---|---|---|---|
| 4,328,318 | 5/1982 | Ray | 128/791 |
| 5,464,446 | 11/1995 | Dreessen et al. | 607/116 |
| 5,843,150 | * 12/1998 | Dreessen et al. | 607/116 |
| 5,865,842 | * 2/1999 | Knuth et al. | 607/116 |
| 5,927,277 | * 7/1999 | Baudino et al. | 607/116 |

OTHER PUBLICATIONS

Medtronic Quad Compact Implant Manual—Model 3887.

* cited by examiner

*Primary Examiner*—Carl H. Layno
(74) *Attorney, Agent, or Firm*—Thomas F. Woods; Michael J. Jaro; Harold Patton

(57) ABSTRACT

A system and method are provided for anchoring a cranial lead or catheter member within a cranial burr hole in a patient, utilizing a feed-through subassembly which permits a lead to be eccentrically positioned with respect to the center of the burr hole, enabling fixation of the lead to the skull while the lead is maintained stereotactically rigid. The feed-through, or anchoring assembly comprises a burr hole element which is positioned within the burr hole, having a radial slit which extends axially through the piece and has a groove for receiving and containing an O-ring, which O-ring is adjustably positioned radially along the slit in accordance with the target position. The O-ring is made of a compressive material, and has a center orifice which closely receives the lead. When the lead is inserted through the O-ring and stereotactically positioned, a clamping element is secured in place above the O-ring, compressing it so as to squeeze it inward, thereby securing the lead while it is still stereotactically fixed.

2 Claims, 6 Drawing Sheets

BURR HOLE CAP FOR FIXATION OF CRANIAL LEAD

FIELD OF THE INVENTION

This invention relates to a cranial lead system and, more particularly, a system and method for affixing a brain lead or catheter which is positioned through a cranial burr hole, so that the lead is secured in position relative to the patient's brain without moving the distal end of the lead.

BACKGROUND OF THE INVENTION

Systems for providing either electrical stimulation of the brain or coupling as fluid to or from the brain are coming into increased use for various purposes. Electrical stimulation of the brain is utilized for relief of chronic pain and treatment of movement disorders. A typical electrical brain stimulation system comprises a pulse generator operatively connected to the brain by a lead. The lead has one or more electrodes at its distal end, designed to be implanted within the patient's brain at a precise location, so that the electrode or electrodes are optimally and safely positioned for the desired stimulation. The lead is connected to the pulse generator at its proximal end, and also needs to be anchored with respect to a burr hole drilled in the patient's skull or cranium, in order to reliably secure the electrodes at the target location. Likewise, in the case of a catheter for providing fluid to the brain or for providing drainage, it is necessary to be able to secure the distal portion of the catheter that passes through the skull and transfers the fluid at a predetermined exact location within the brain. Still further, for a combined catheter and lead member, such secure and reliable anchoring of the member so that the distal end is precisely located within the skull, is very important. As used herein, the term lead, or lead-type member, refers to any such cranial catheter or lead.

Reference is made to U.S. Pat. No. 5,464,446, "Brain Lead Anchoring System," assigned to Medtronic, Inc., which is incorporated herein by reference. The referenced patent illustrates an effective lead anchoring system, and it discusses the method of providing access through the skull by drilling a burr hole with a cranial drill, inserting a stimulation lead through the burr hole and positioning it so that the electrode or electrodes are at the desired stimulation site. The lead is positioned using a stereotactic instrument, which permits a very precise movement within the brain. Once the lead is positioned and tested to determine that the results of stimulation are satisfactory, it is critical that the lead is not moved, since even a small displacement can result in less than optimal results, and even injury to the brain. Accuracy should be maintained with ±0.5 mm.

The anchoring system of the '446 patent shows a basic anchor for fixing the lead in place with the distal portion extended through the cranial burr hole, and then securing it by bending it into a slit such that it is held by a friction fit. However, the lead must first be removed from the stereotactic instrument, such that this system does not provide a reliable way for accurately securing the lead, or catheter, before it is bent into the fixation position. Thus, such a system does not reliably preclude a small movement of the distal end of the lead at the time of fixating, or securing the lead in place. Rather, it is required that the lead be removed from the stereotactic device before the lead can be fixed to the skull.

In U.S. application Ser. No. 08/705,566, filed Aug. 29, 1996, assigned to the same assignee as this invention, there is shown an apparatus and method wherein a compression screw cap is screwed down onto a compressible seal, the seal being flexible and compressed laterally against the outer wall of the lead. This system provides a substantial improvement over the prior art, and in particular enables securing the lead with respect to the skull before it is stereotactically released. However, it is operative only when the lead is to be positioned in the center of the burr hole. If, however, the target localization procedure indicates that the lead must be inserted off-center, this assembly and the procedure of using it is not adequate; the lead must be bent in order to fix it through the iso-centric burr hole cap, and this bending results in a lead displacement from the stereotactically determined target. There thus remains a need in the art for a reliable system which enables off-center, or eccentric placement of the lead through the burr hole, without requiring stereotactic release of the lead.

SUMMARY OF THE INVENTION

It is an object of this invention to provide a brain treatment system, having a fixation subassembly and procedure for fixing a brain lead off-center, or eccentric from the center axis of the burr hole in the patient's skull. This objective is to be met without stereotactic release of the lead, so that the lead is secured to the patient's brain without displacement of the lead distal end from the stereotactically determined target.

There is provided a system and method for electrical and/or fluid treatment of a patient's brain, having a subsystem for anchoring a lead or a fluid catheter within a cranial burr hole within a patient's skull, wherein the anchoring subsystem has a feed-through burr hole piece, and an adjustable compressive element through which the lead is positioned. The compressible element is movable laterally so that it can be positioned to the required off-center position that has been identified by the target localization procedure. The burr hole feed-through piece contains a radial slit through which the lead passes, the slit further having an upper grooved portion for receiving a compressible O-ring. A compression plate is placed over the O-ring, and pressed down thereupon by a clamping screw, causing compression of the O-ring and radially inward compressive force on the lead outer surface, thereby securing the lead in place with respect to the skull while it is still being stereotactically held. Following fixation by the compressive O-ring, the lead is released from the stereotactic instrument and secured through a burr hole cap, the proximal end of the lead then being connected to an implantable stimulator device or pump.

DESCRIPTION OF THE PREFERRED EMBODIMENTS

Figure 1:
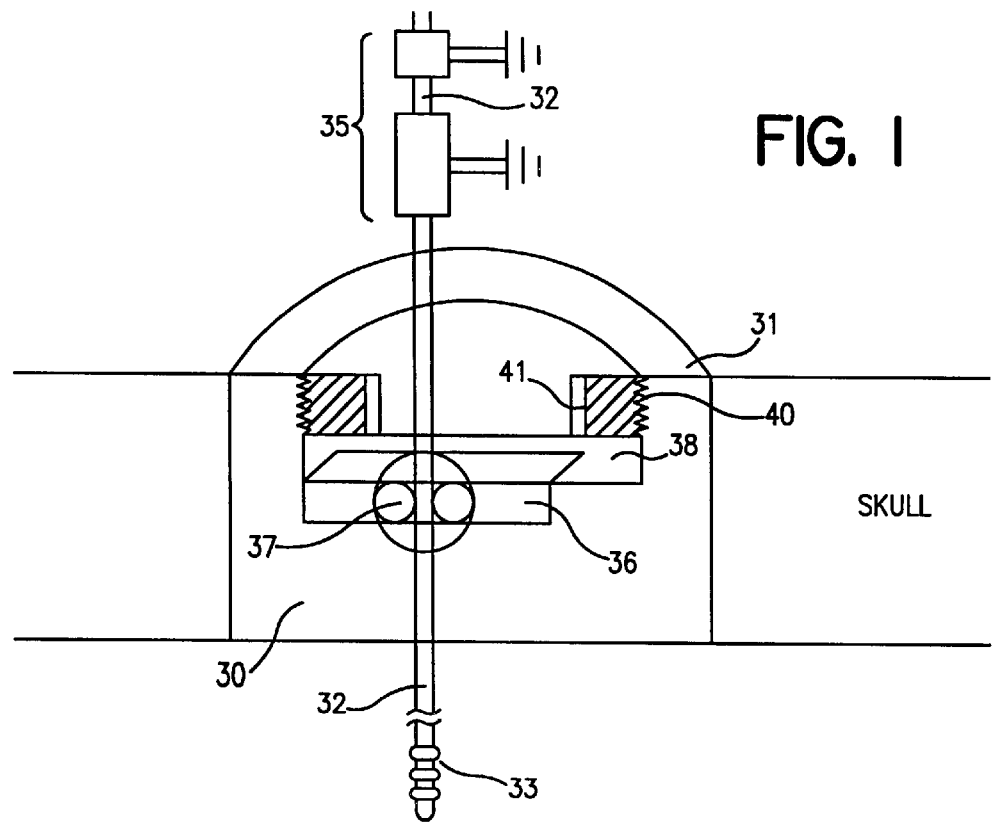
FIG. 1 is a cross-sectional view of the anchoring subassembly of this system, showing a lead being stereotactically held in position, the lead being passed through the anchoring subassembly.

Referring now to FIG. 1, there is shown a cross-sectional view illustrating the main components of the burr hole assembly portion of this invention. This drawing is intended to be illustrative, and is not necessarily to scale. A burr hole piece, or element 30 is positioned within a burr hole which has been drilled in the patient's skull in a known manner. The piece 30 is affixed to the skull in a conventional manner, e.g., by suturing. A lead, or catheter 32 is shown positioned through the burr hole piece, and held stereotactically by a stereotactic member 35, shown schematically. For an embodiment which utilizes a cranial lead for providing stimulation, the lead carries electrodes positioned at the distal end portion, as indicated at 33. For an embodiment where fluid is pumped to or withdrawn from the brain, the catheter 32 has an axial lumen for carrying the fluid. As used in this specification, the term "lead" embraces a lead for transmitting stimuli to the brain, and also includes a catheter or combination lead and catheter, and is not limited to any one specific type element.

Figure 5:
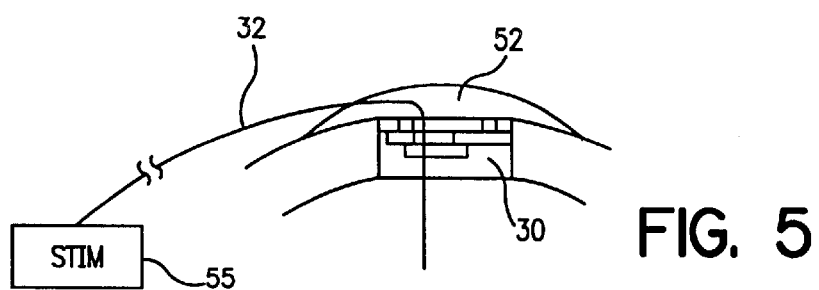
FIG. 5 is a diagram illustrating the fixation subassembly of this invention in position in a patient's skull, and illustrating the lead connected to a stimulator or a pump device.

As seen in FIG. 1, the lead 32 is displaced off-center from the central axis of the burr hole, i.e., it is eccentric with respect to the burr hole. As discussed above, the target localization procedure may determine that the proper target does not lie on the center axis of the burr hole which has been drilled, and as a consequence the lead must be positioned off-center. Burr hole piece 30 has a slit portion shown at 36, wherein is placed an O-ring 37, which squeezes radially inward to grip lead 32, in a manner described in more detail below. An annular opening at 38 receives a compression plate 44, which in turn is clamped by clamping screw 41, which is screwed into piece 30 on threads 40. The downward force of plate 44 compresses the O-ring, which is largely contained within slit 36, such that the O-ring material, e.g., silicone rubber, compresses radially inward and grips lead 32. When this has been achieved, the lead can be removed from the stereotactic member 35, and connected to a stimulator or flow delivery device 55, as illustrated in FIG. 5.

Figure 2:
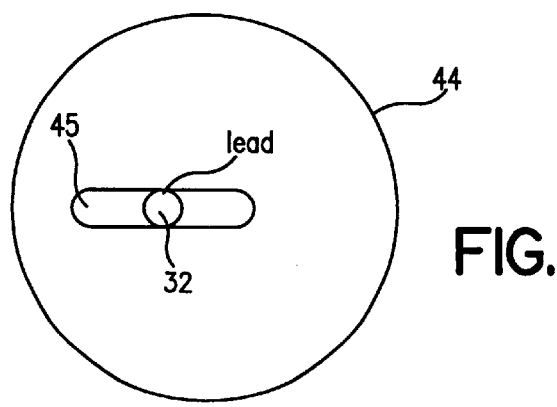
FIG. 2 is a top diagrammatic view of the plate that provides downward pressure on the compressive O-ring, in accordance with the invention.

Referring to FIG. 2, there is shown a top diagrammatic view of plate 44, which is laid down on top of O-ring 37. Plate 44 has a slit 45, which runs from about the center axis of the plate radially toward the circumference, having a width which is just larger than the outer circumference of lead 32. When placing the lead through to the brain, both piece 30 and plate 44 are rotated, so that the slits line up at the correct angle to permit placement of the lead 32 through to the proper position in the brain.

Figure 3A:
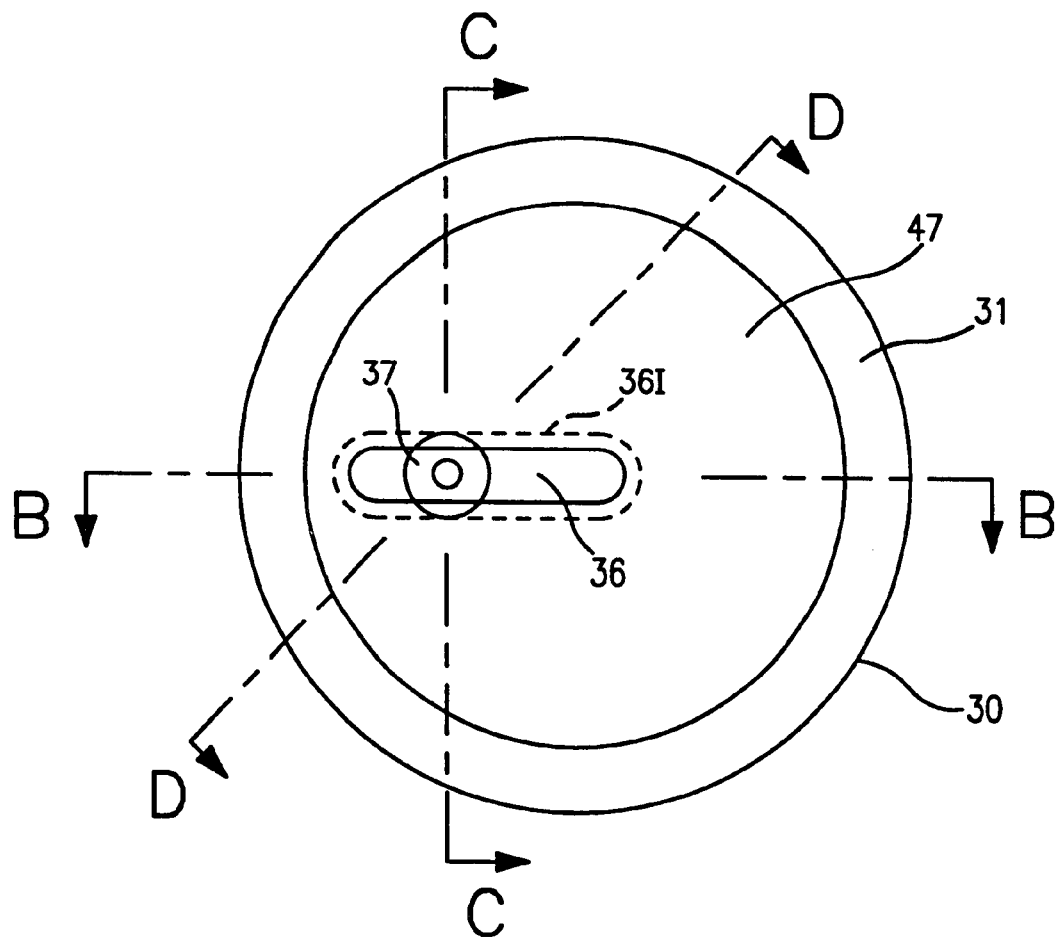
FIG. 3A is a top diagrammatic view of the burr hole feed-through piece of this invention, illustrating the slit which is configured to retain the adjustable O-ring and provide for eccentric anchoring of the lead.
Figure 3B:
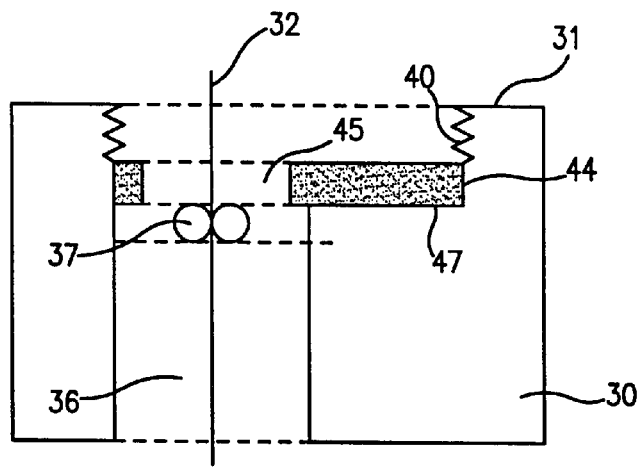
FIG. 3B is a cross-sectional view taken across lines B—B of FIG. 3A, also showing placement of the compression plate.
Figure 3C:
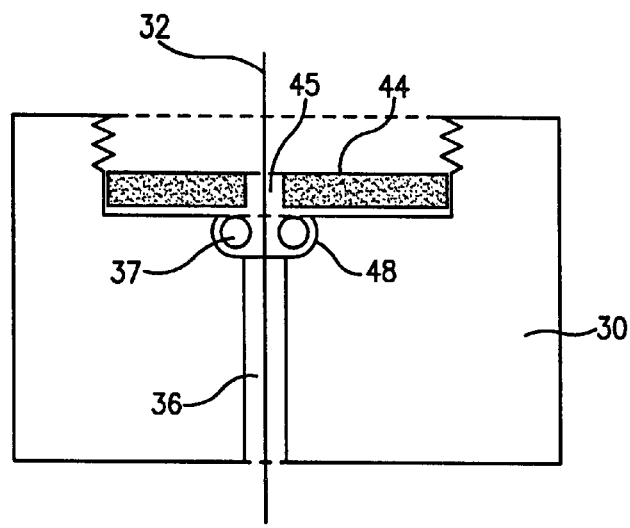
FIG. 3C is a cross-sectional view of the burr hole feed-through piece taken along lines C—C of FIG. 3A, also showing the compression plate in position.
Figure 3D:
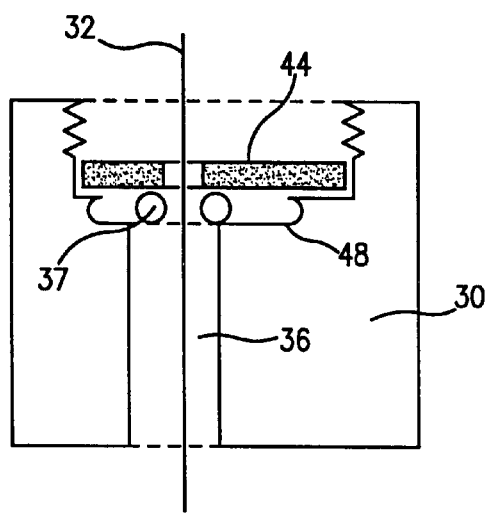
FIG. 3D is a cross-sectional view of the burr hole feed-through piece taken along lines D—D of FIG. 3A, also showing the compression plate.

Referring now to FIGS. 3A–3D, the important features of a first embodiment of the burr hole piece 30 and the plate 44, for enabling an eccentric placement of lead 32, are shown. It is noted that these figures are illustrative of the concepts and elements of the invention, but are not exactly drawn to scale. By way of reference, the burr hole piece 30 may have, e.g. a diameter of 14 mm; and lead 32 has a typical diameter of about 1.3 mm. Referring to FIG. 3A, there is seen a top view, looking in the direction down through the top of the patients skull, at the burr hole element which is positioned within the burr hole. The element is preferably a solid piece of machined metal. A top edge 31, seen also in FIGS. 3B–3D, is substantially flush with the top of the skull when piece 30 is placed and secured within the burr hole. Within top edge 31 there is a surface 47, within which is drilled slit 36 which extends to the bottom of the burr hole piece. Slit 36 has top width somewhat less than the diameter of O-ring 37; and has an inner recessed groove shown at 48 in FIGS. 3C and 3D, which containingly receives the O-ring 37. The inner edge of groove 48 is also shown by the dashed line 36I in FIG. 3A.

FIG. 3B shows a cross-section of burr-hole piece 30 which is taken through the center and along the slit, as indicated at B—B in FIG. 3A. This view also includes plate 44, having its slit 45 lined up to coincide with slit 36. As seen, slit 36 extends to the bottom of element 30, and is eccentric with respect to the center axis of element 30. Plate 44 is shown in position, lying on surface 47, having plate slit 45 aligned with burr hole piece slit 36. The center axis of lead 32 is shown positioned through the center of O-ring 37. Referring to FIG. 3C, the view is taken along cross-section C—C indicated in FIG. 3A, meaning that the view is in the direction of slits 36 and 45. In this case, slit 36 is seen as a narrow width, being just large enough to accommodate the lead 32. Note that in this view also the slit 45 of plate 44 has a width that is just sufficient to accommodate lead 32. Note also the containing groove or contour 48 of slit 36, which receives the O-ring 37. This groove is configured to match the outer geometry of the O-ring, so that the O-ring is held in place when plate 44 is pressed downward. This groove also holds the small O-ring in place while, e.g., in the package during transportation or during handling by the doctor, whereby there are no loose components that can be lost. FIG. 3D provides yet another view of the same embodiment, showing an off-center view indicating slit 36 with the upper portion thereof defined by containing surface 48.

Figure 3E:
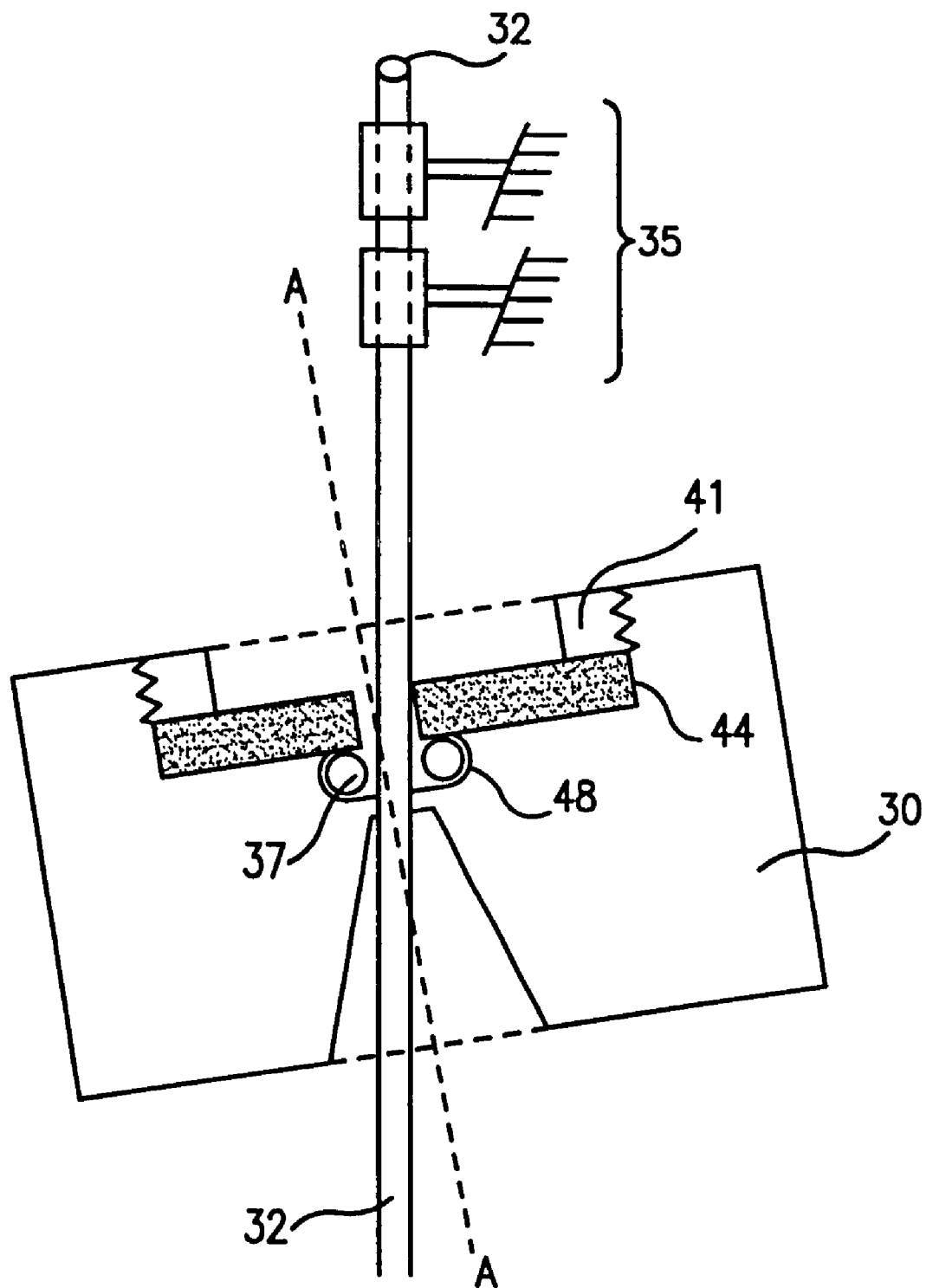
FIG. 3E is a cross-sectional view similar to FIG. 3C, of an alternate embodiment whereby the lead can be placed at an angle to the burr hole piece axis.

Referring now to FIG. 3E, there is shown a view similar to that of FIG. 3C, but illustrating an alternate embodiment which enables placement of the lead 32 at an angle with respect to the axis of the burr hole piece. As seen, slit 36 has tapered walls 36', which enables placement of the lead 32 at an angle with respect to burr hole and the axis (A—A) of the burr hole piece 30. Thus, as illustrated, the lead 32 is positioned by the instrument 35 to be at an angle to the axis which is perpendicular to the top of the skull, thereby providing increased flexibility in directing the lead to the desired brain location. Stated in another way, the direction of the lead can be offset from the perpendicular to the burr hole ring piece.

Figure 4A:
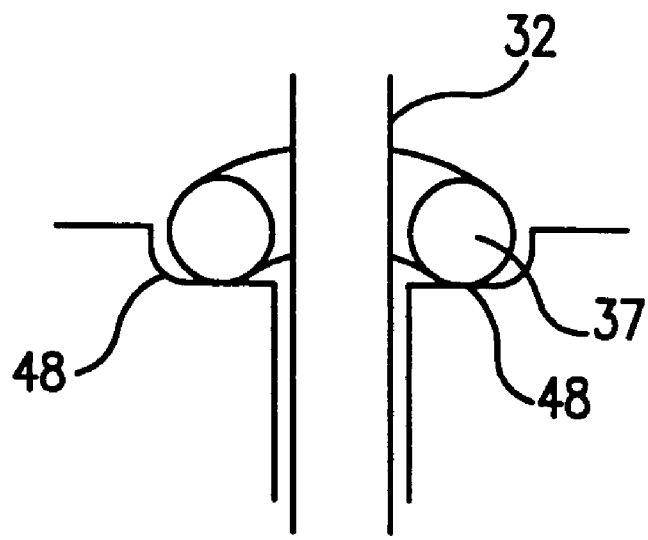
FIG. 4A is a diagrammatic view showing the O-ring in position within the retaining groove of the slit in the burr hole piece, with the lead positioned through the center opening of the O-ring, and without any downward force on the O-ring.
Figure 4B:
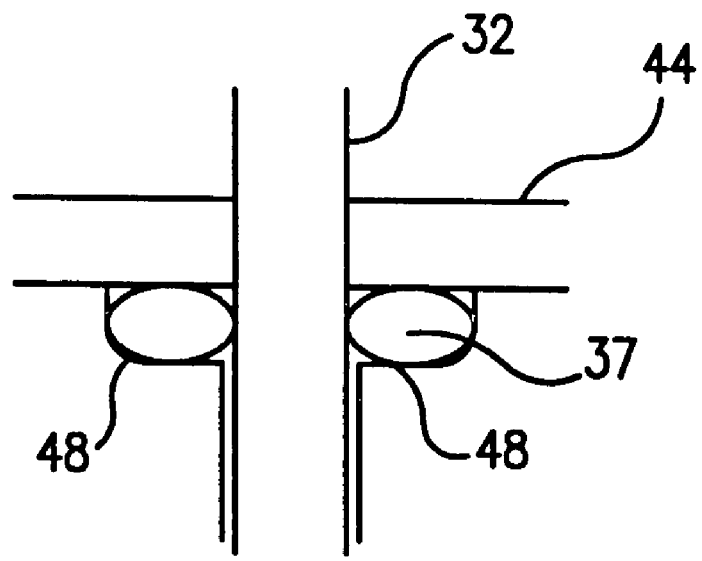
FIG. 4B is a diagrammatic view the same as FIG. 4A, but with the plate providing downward compression on the O-ring, illustrating the inward compressive force by the O-ring which fixes lead 32.

FIGS. 4A and 4B provide a diagrammatic representation of the compressive force of O-ring 47. Without the plate 44 in position, as shown in FIG. 4A, O-ring 37 fits somewhat loosely in the groove defined by surface 48, and is not engaging lead 32 which has been positioned through the center of the O-ring. In FIG. 4B, with the compressive plate 44 in position and exerting a downward force, O-ring 37 is squeezed tightly into the cavity provided by groove surface 48, with a resulting radially inward compressive force which securely grips lead 32, and holds it in position. The O-ring is preferably made of silicone rubber, but can be made of other materials, and can have a doughnut or other ring-shaped geometry.

As seen in FIG. 5, after the lead has been secured within burr hole element 30 by the O-ring, it is released from the stereotactic instrument and passed through a surface cap 52, and connected to an implantable stimulator or pump device 55, for chronic operation. Cap 52 may be any conventionally used cap, and may provide an upper surface which is substantially flush with the patient's skull. Cap 52 conventionally has a pathway for passing the lead 32 laterally to the side of the burr hole, from which position it is then connected to device 55. Cap 52 and piece 30 are suitably used as shown in U.S. Pat. No. 5,464,446, for passing the lead laterally. As used herein, device 55 communicates with the patient's brain, either by delivering stimulus pulses or pumping fluid through lead 32.

Figure 6:
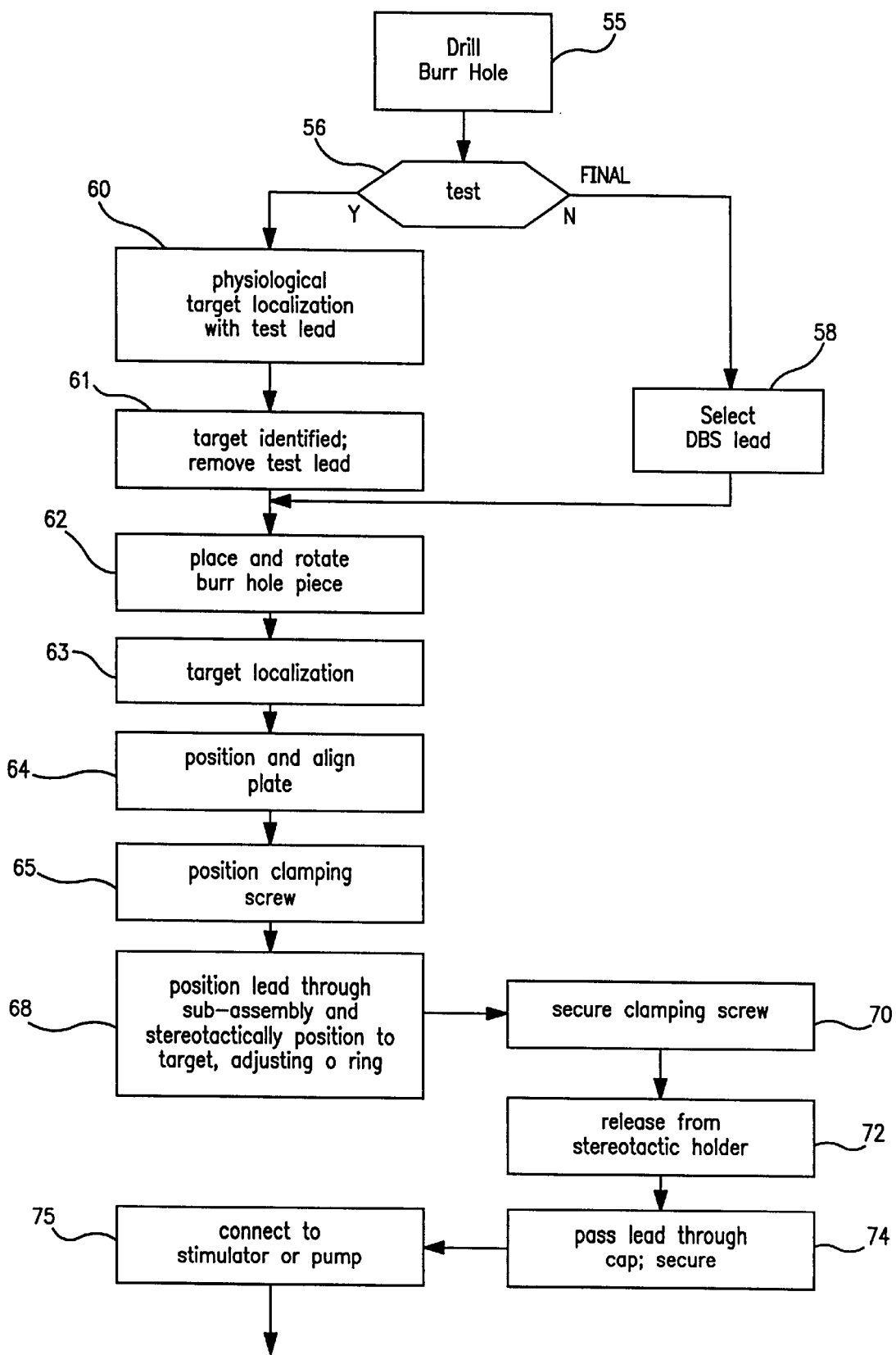
FIG. 6 is a flow diagram illustrating the primary steps taken in carrying out the procedure of this invention, either for a test lead or for the final DBS lead.

Referring to FIG. 6, there are shown the primary steps of the method and technique of securing the lead 32 in accordance with this invention. Initially, as indicated at 55, the burr hole is drilled in the patient's skull, using known techniques. It is determined whether the procedure is to use a test lead, or the final procedure of implanting the DBS lead, as indicated at 56, 58. For the initial test lead, at 60 physiological target localization is performed. At 61, the target is identified, and the test lead is removed. Then, at 62, the burr hole piece is placed and rotated to the proper angle, so that the slit 36 provides entry of the lead 32 to the proper location. Following this, as seen at 63, for either a test lead or DBS type lead, target localization is performed, to position the lead properly with respect to the brain portion which is to be stimulated, or to which fluid is to be delivered. See, for example, U.S. Pat. No. 5,843,150, filed Oct. 8, 1997. At 64, 65, the loose plate 44 and clamping element 41 are positioned loosely over the lead. The lead then is passed down through the burr hole assembly and stereotactically positioned at the correct position, as indicated at 68. When the correct position has been confirmed, the loose plate is placed in position on surface 47, and the clamping element is screwed into place, as indicated at 70. When this is done, as explained above, the O-ring secures the lead in the proper position, without movement of the distal tip. Following this, at 72 the lead is released from the stereotactic instrument, and at 74 the lead is passed through the upper cap 52, which cap is then secured to the patient's skull. Finally, at 75, the lead is connected to the stimulator or pump device 75, to complete installation of the system.

The burr hole fixation assembly of this invention allows reproducible, non-destructive release of lead 32 from its fixed condition, by unscrewing clamping screw 41. This feature is very important if, for whatever reason, it is necessary to reposition lead 32. Thus, stereotactic repositioning can be carried out simply by proceeding backward at any point in the procedure illustrated by FIG. 6, fixing the lead position, and then proceeding forward again.

What is claimed is:

1. A system for communicating with a patient's brain comprising an implantable device, a lead for interconnecting said device and the patient's brain, said lead being tubular with an outer diameter, and a subsystem for holding said lead in position relative to the patient's skull, the subsystem being positioned in a substantially cylindrical burr hole drilled in the patient's skull, said burr hole having a center axis, the subsystem further comprising:

eccentric means for enabling passage of said lead through said burr hole at an off-center location; and clamping means for clamping said lead in a said off-center position with respect to said burr hole without significant movement of said lead, wherein said eccentric means comprises a feedthrough piece secured within said burr hole, said piece having a receiving groove extending radially and transversely to the center axis of said burr hole, and a ring-shaped element slidably positioned in said receiving groove, said feedthrough piece having a first radial slit that extends axially through said piece, said groove being positioned at the top of said slit, said clamping means comprising a compression disc having a radial slit in alignment with said first radial slit, said feedthrough piece further having a slit which tapers radially outward from top to bottom, thereby permitting positioning of the lead at an angle with respect to the axis of said piece.

2. A sub-system for affixing a brain lead to a patient's skull, comprising:

a substantially cylindrical burr hole piece which fits within a burr hole in said patient's skull;

lateral means positioned within said burr hole piece for receiving said lead at an adjustable radial location relative to the center axis of said burr hole piece; and clamping means for clamping said lead at said adjustable location, thereby fixing said lead relative to said burr hole, and tapering means for permitting said lead to be positioned and fixed at an angle relative to the axis of said burr hole.

* * * * *